United States Patent [19]
Elliott et al.

[11] Patent Number: 5,935,859
[45] Date of Patent: Aug. 10, 1999

[54] APPARATUS AND PROCESS FOR ARRAYING BEADS

[75] Inventors: John Duncan Elliott, Wayne; John Gerald Gleason, Downingtown; Jack Dale Leber, Doylestown; Gerald C. Simolike, Sharon Hill, all of Pa.

[73] Assignee: SmithKline Beecham Corporation, Philadelphia, Pa.

[21] Appl. No.: 09/124,802

[22] Filed: Jul. 29, 1998

Related U.S. Application Data

[63] Continuation of application No. 08/785,072, Jan. 17, 1997, abandoned.

[51] Int. Cl.⁶ .................................................. G01N 35/10
[52] U.S. Cl. ........................... 436/54; 436/49; 436/180; 422/63; 422/81; 422/100
[58] Field of Search ................................ 422/63, 65, 67, 422/81, 100, 104; 636/43, 47, 69, 54, 174, 180

[56] References Cited

U.S. PATENT DOCUMENTS

| | | | |
|---|---|---|---|
| 4,401,456 | 8/1983 | Connick, Jr. ................................. | 71/88 |
| 4,681,742 | 7/1987 | Johnson et al. ........................... | 422/102 |
| 4,685,480 | 8/1987 | Eck .......................................... | 134/182 |
| 4,754,771 | 7/1988 | Tangherlini et al. ..................... | 134/102 |
| 4,767,600 | 8/1988 | Vicario ...................................... | 422/65 |
| 4,879,242 | 11/1989 | Tsukioka .................................. | 436/54 |
| 4,913,179 | 4/1990 | Engel et al. ............................. | 134/113 |
| 4,937,048 | 6/1990 | Sakai et al. ............................. | 422/63 |
| 5,183,638 | 2/1993 | Wakatake ................................ | 422/64 |
| 5,185,269 | 2/1993 | Wells ....................................... | 436/180 |

*Primary Examiner*—Long V. Le
*Attorney, Agent, or Firm*—Stephen A. Venetianer; William T. King; Charles M. Kinzig

[57] ABSTRACT

A mixture of beads from a combinatorial library is held in suspension either by inducing circulating flow of a liquid in a tapered vessel by rising air bubbles or by floating the beads at the interface between two immiscible liquids. Beads are selected individually from the suspension by drawing liquid into the tip of a needle having a circular opening smaller than the diameter of a bead. After a bead is captured on the tip of a needle, excess beads are jarred loose or washed away by flow of a solvent through a sheath surrounding the needle, and the needle is moved by a robotic manipulator to a well into which the bead is released.

17 Claims, 5 Drawing Sheets

APPARATUS AND PROCESS FOR ARRAYING BEADS

CROSS-REFERENCE TO RELATED APPLICATIONS

This is a continuation of application Ser. No. 08/785,072 filed Jan. 17, 1997, now abandoned.

FIELD OF THE INVENTION

This invention relates generally to the handling of beads and more particularly to an improved process and apparatus for depositing such beads in two-dimensional arrays.

BACKGROUND OF THE INVENTION

Synthesis of combinatorial compound libraries on bead supports is a well-established method for generating chemical diversity for screening against targets of pharmacological relevance. Such libraries may be synthesized as bulk populations or discrete sublibraries with or without identifier tags for deconvolution. In most cases each bead carries a single unique compound and is present in a mixture of beads containing other compounds. To test the beads for activity against a pharmacological target, it is desirable to separate the beads so that each bead may be individually assayed against one or more targets. The beads carrying active compounds can be identified and the structures of the compounds elucidated. It is also desirable to separate the beads into arrays that are geometrically compatible with robotic screening systems, for example 8×12 arrays or other formats such as 384 or 896-well configurations.

Current methods of bead arraying include manual picking and hydrodynamic sorting in which beads are allowed to flow though an aperture and once detected are deposited into assay wells. Manual picking is slow and tedious. Hydrodynamic methods heretofore in use have been slow and the equipment is prone to clogging. Buoyancy variations within the bead library are also known to cause problems in hydrodynamic sorting. A problem common to the prior methods is that, because the beads are extremely small, typically 300 m (0.3 mm) or smaller, there is a tendency for two or more beads, carrying different compounds, to be deposited occasionally at a single location in the array. Still another problem encountered in bead arraying is that the beads tend to be fragile, and can be broken up into fragments especially when mechanically agitated.

There is a need for a simple, rapid and reliable method and apparatus for bead arraying which reliably delivers a single bead to each point in the array. The principal object of this invention, therefore, is to provide an improved apparatus and method for selecting individual compound-bearing beads from a combinatorial library and reliably depositing individual beads into an array. It is also an object of the invention to provide an improved apparatus for bead arraying which is inexpensive, easy to use and independent of the nature of the compounds on the beads. Still another object of the invention is to avoid, or at least reduce instances in which the beads are broken up into fragments.

SUMMARY OF THE INVENTION

In accordance with the invention, liquid is drawn, from a vessel containing a mixture of beads suspended in a liquid, into an internal passage of a hollow, movable pick-up element, preferably a needle, through an opening at an end of the internal passage. The opening is of a size smaller than any of the beads and, at least in the case of spherical beads, the opening is preferably circular in shape so that it can be substantially closed off by a bead. When a bead closes off the opening, a pressure differential is maintained so that the external pressure exerted on the bead is greater than the pressure within the passage. The pressure differential holds the bead in engagement with the opening. While the pressure differential is maintained, the movable pick-up element is withdrawn from the vessel with the bead held in engagement with its opening, and the bead is deposited at a location remote from the vessel by releasing the bead from the opening.

The technique in which a bead is selected by drawing liquid into a passage, and the bead is held to the opening of the passage by a pressure differential, reduces the instances of deposition of multiple beads at a given array location. However, still further improvements are achievable by techniques for dislodging any beads adhering to the movable pick-up element other than the bead closing off the opening. One such technique is to jar the movable element.

Another technique for ensuring that only single beads are deposited is to cause a flow of a fluid over at least a part of the movable element to dislodge any unwanted beads. A preferred way to wash off excess beads is to cause a fluid to flow through an annular passage formed by a sheath surrounding a hollow needle which provides the internal passage.

Beads used in combinatorial chemistry are typically very fragile. Therefore in keeping the beads in suspension so that they can be picked up by the flow of liquid into the hollow, movable element, it is important to prevent the beads from being broken up. This may be done in either of two ways in accordance with the invention.

A first technique is to hold the beads of the mixture in suspension in the liquid by introducing a flow of gas into the vessel to produce gas bubbles therein. Preferably, at least a portion of the interior of the vessel extending upwardly from the bottom thereof has a continuously increasing horizontal cross-section in the upward direction. The beads of the mixture may be held in suspension in the liquid by introducing a flow of gas into the liquid in the vessel at the bottom thereof to produce rising gas bubbles in the liquid, which gently circulate the beads so that they do not collide, with one another or with the vessel walls, with such force that they are broken up into fragments.

In an alternative technique, the liquid in which the beads are suspended comprises two immiscible liquid components, one component floating on the other. The density of the beads is higher than the density of the one component and lower than the density of the other component, and consequently the beads are suspended at the interface of the two components. The drawing of liquid into the internal passage of the hollow movable element is carried out as the opening at the end of the internal passage is moved through the interface.

The apparatus used in accordance with the invention also lends itself to a simple procedure to detect clogging of the opening or of the internal passage of the hollow movable element. To detect clogging, pressure is applied to gas in the internal passage, and clogging is detected by sensing the absence of flow, or the diminished flow, of gas through the opening in response to the applied pressure.

As will be seen in the following detailed description, the invention provides a simple, inexpensive and easily used method and apparatus for achieving highly reliable selection of individual beads from a mixture of compound-bearing beads, and deposition of the selected beads into an array while reducing or substantially eliminating the undesirable deposition of multiple beads at a single array point.

Various other objects, details and advantages of the invention will be apparent from the following detailed description, when read in conjunction with the drawings.

DETAILED DESCRIPTION

The invention preferably utilizes a modified robotic sample processor. A suitable processor, sold under the trademark GENESIS, is available from Tecan U.S. Inc., P.O. Box 1395, Research Triangle Park, N.C. 27709, U.S.A. The processor is depicted schematically in FIG. 1. It comprises a worktable 10 and a traveling robotic manipulator arm 12, which is movable horizontally above the worktable. Within the arm, a carriage 14 is movable horizontally in a direction perpendicular to the arm movement. The carriage supports a series of pipettes 16, which are vertically movable in sleeves 18 on the carriage. The horizontal movements of the arm and carriage and the vertical movements of the pipettes are under microprocessor control. Thus, the movement of the pipettes can be controlled in three dimensions, for automated handling of liquid samples. The pipettes are connected to microprocessor-controlled fluid pumps (not shown in FIG. 1) through flexible tubes 20.

Figure 1:
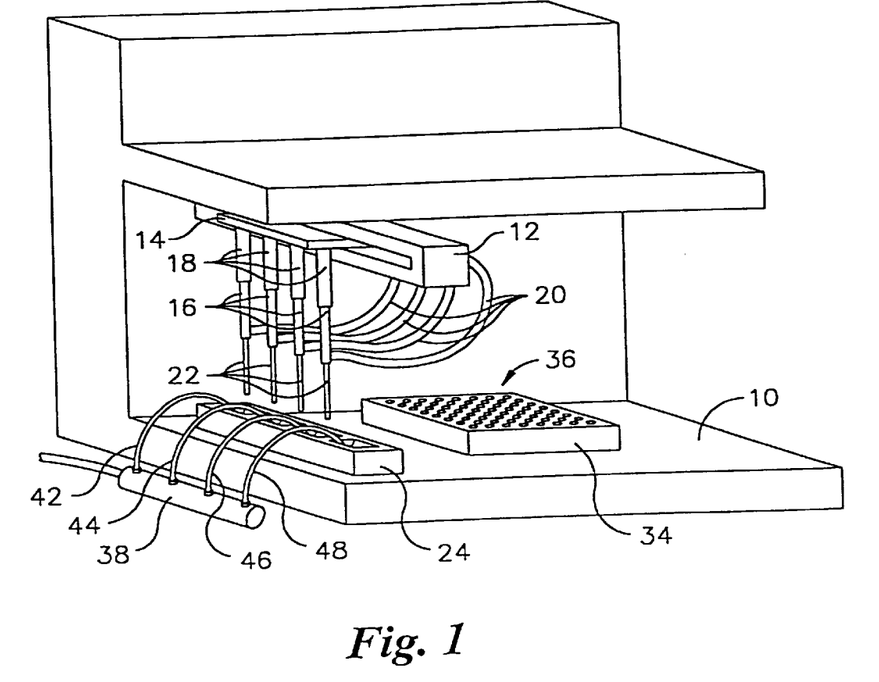
FIG. 1 is a perspective schematic view of a robotic sample processor used to carry out the process of the invention.

To carry out the arraying process of this invention, the sample processor is modified by fitting the pipettes with hollow needles 22. A suitable needle for use in arraying spherical polystyrene beads 230 m in diameter is a hypodermic needle having a size in the range of 25–30 gauge, with its tip ground to provide a circular opening in a plane perpendicular to the axis of elongation of the needle. Thus, the opening at the tip of the needle has a diameter less than that of the beads to be arrayed, and the circular configuration of the opening makes it possible for a spherical bead to close off the opening substantially completely.

A tray 24, from which the needles pick up beads, is provided on the worktable. The tray shown has four separate compartments (shown as compartments 26, 28, 30 and 32 in FIG. 2). These compartments are spaced from one another other at intervals such that the needles 22 can enter them simultaneously.

Also situated on the worktable is a conventional well plate 34 into which beads are deposited by the needles. The well plate has an array 36, typically comprising ninety-six wells in an 8×12 array. The spacing of the needles 22 may be such that they can enter every second well in each row of wells in the well plate. Therefore, to serve all eight wells in a row, the needles first deposit beads in the first, third, fifth and seventh wells. Then after returning to the tray 24 to pick up four additional beads, the needles are indexed, by movement of carriage 14, so that they are in a position to deposit beads in the second, fourth, sixth and eighth wells.

Figure 2:
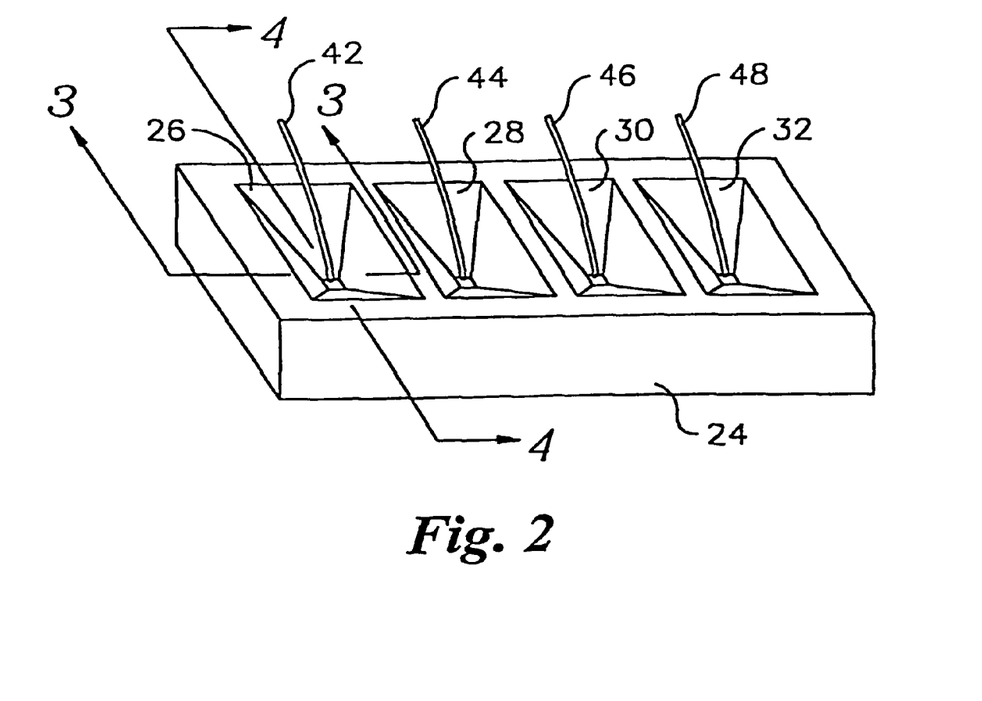
FIG. 2 is a perspective view of a suspension holder.
Figure 3:
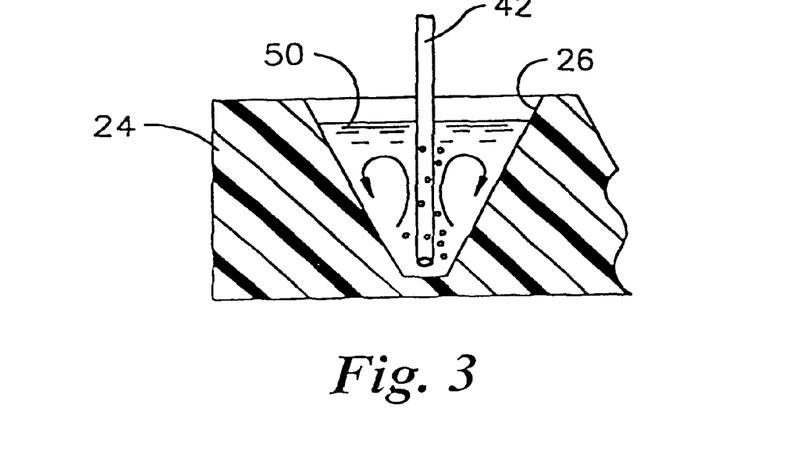
FIG. 3 is a fragmentary sectional view of the suspension holder taken on plane 3—3 of FIG. 2, illustrating the use of bubbles to maintain particles in suspension.

Also shown in FIG. 1 is a manifold 38, which is used to distribute a gas, such as nitrogen, from a supply line 40 to the compartments of tray 24 through conduits 42, 44, 46 and 48. As shown in FIG. 2, each of compartments 26–32 has sloping sidewalls which diverge from one another, proceeding upwardly from a narrow bottom, so that the horizontal cross section increases continuously in the upward direction. Each of the conduits 42–48 extends along one of the sloping sidewalls of its compartment to a location immediately adjacent the bottom of the compartment, where it is able to release gas bubbles into the liquid in the compartment, as shown in FIGS. 2 and 3. The liquid 50 in each compartment is typically a solution consisting of 20% methanol and 80% water (by volume). Polystyrene beads, especially beads to which compounds are attached, have a density slightly greater than the density of this solution and would ordinarily sink to the bottom. However, the rising bubbles of gas induce a circulating flow of liquid, as depicted by the arrows in FIGS. 2 and 3. The circulating flow lifts beads from the bottom of each compartment, and keeps them in suspension. The tapered shape of each compartment ensures that there are no stagnant locations at which beads can collect.

Figure 4:
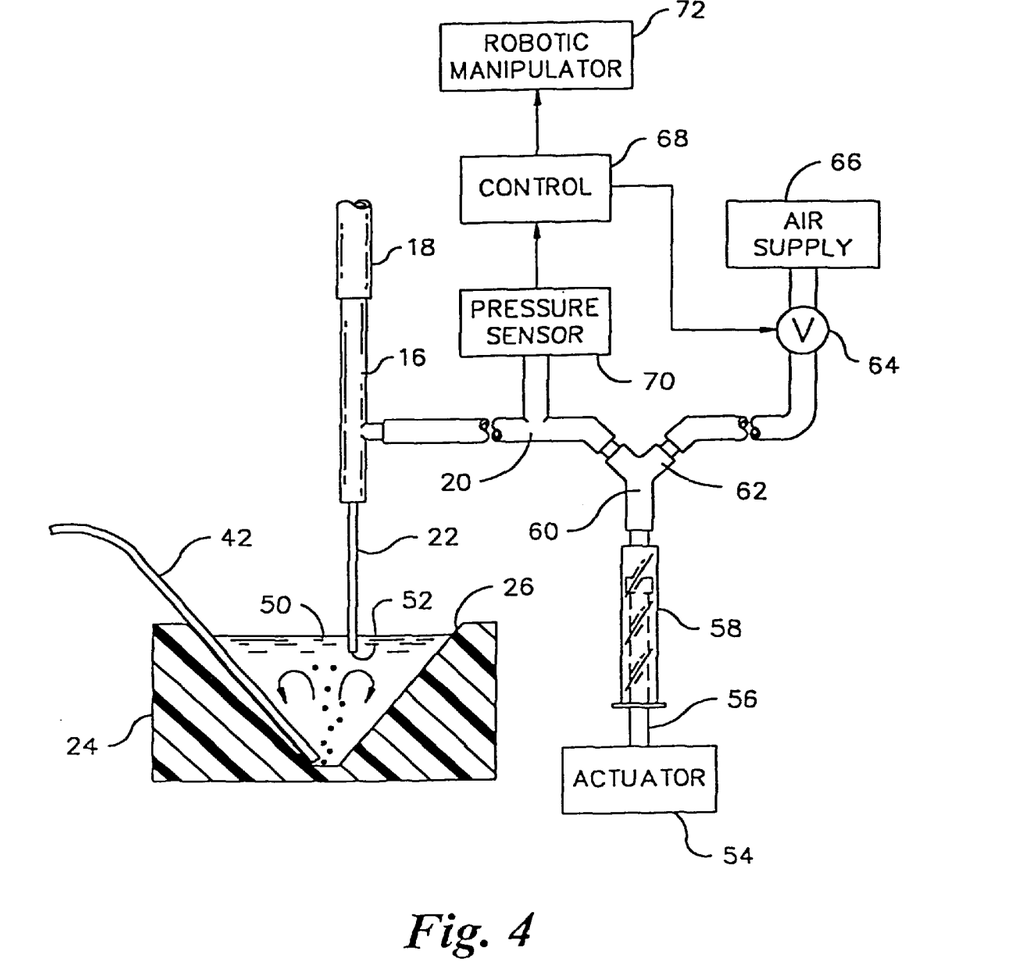
FIG. 4 is a fragmentary sectional view of the suspension holder taken on plane 4—4 of FIG. 2.

As shown in FIG. 4, the end 52 of a needle 22 is inserted into the liquid 50 in compartment 26. A mechanical actuator 54, under microprocessor control, operates the plunger 56 of a syringe 58, the interior of which is connected to the pipette 16 through flexible tube 20 by way of a Y-connection 60. The other branch 62 of the Y-connection is connected through a valve 64 to an air supply 66. The valve is operated by a control 68 to connect the air supply to the needle. A pressure increase in branch 62 resulting from the clogging of the needle can be detected by a pressure sensor 70, which can provide a signal to notify the operator, or to take the needle out of service automatically.

Figure 5:
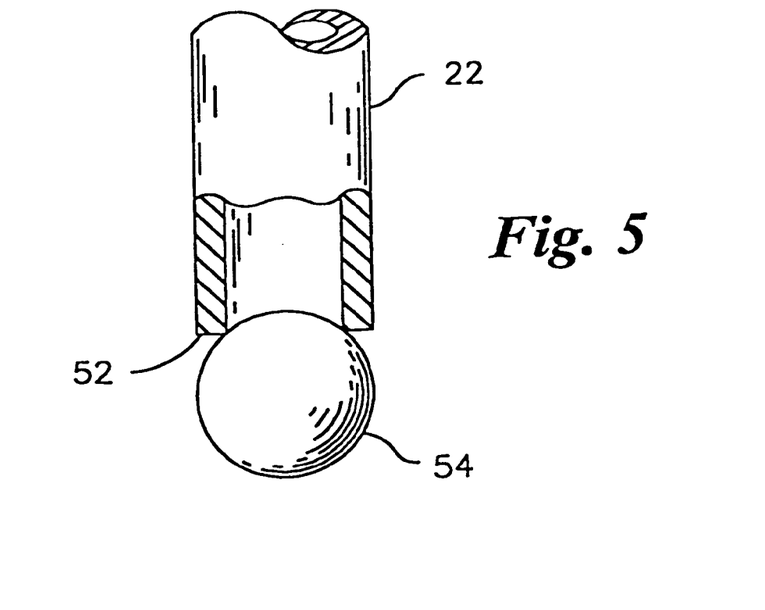
FIG. 5 is a fragmentary sectional view showing a needle holding a bead.

The withdrawal of the plunger 56 by actuator 54 draws liquid 50 into needle 22. The maximum amount of liquid is limited by the stroke of the plunger and the capacity of the syringe. For example the amount of liquid drawn into the needle can be limited to 200 L. As liquid flows into needle 22 one of the beads in the suspension, in the vicinity of the tip 52 of the needle, will ultimately be drawn against the opening at the tip of the needle. When the bead 54 closes the opening, as depicted in FIG. 5, further withdrawal of the plunger 56 of syringe 58 reduces the pressure of the air within the syringe, and line 60, and any air remaining within the pipette 16 or the needle 22. The resultant differential between the external pressure in the liquid at the tip of the needle (which is essentially atmospheric), and the internal pressure within the needle, holds the bead against the tip of the needle, so that it can be carried by the needle to one of the wells in well plate 34 (FIG. 1). The pressure decrease within the needle, which occurs when a bead is captured at the tip of the needle, is also detected by pressure sensor 70, which delivers a signal to control 68. Signals from pressure sensors associated with all of the needles are processed by control 68, which operates the robotic manipulator 72 to move the needles from the tray 24 to the well plate 34 when beads have been captured by all of the needles that are in service.

The apparatus depicted in FIGS. 1–5 draws liquid into needles, capturing beads at the tips of the needles. The captured beads are transported to a well plate and deposited individually in selected wells by reverse operation of the plungers of syringe 58 and its counterparts associated with the other needles.

Occasionally more than one bead may adhere to a needle as it is withdrawn from the tray 24. When this occurs, typically one or more excess beads adhere to the bead captured at the tip of a needle. Since the presence of beads containing different compounds in the same well is undesirable, it is important to ensure that only one bead is deposited in each well. Therefore, any excess beads can be shaken loose before the needles are moved to the vicinity of the well plate. To eliminate excess beads, the manipulator arm can be stopped suddenly, or the needles can be brought into contact with a stop (not shown) to jar the excess beads loose.

Figure 6:
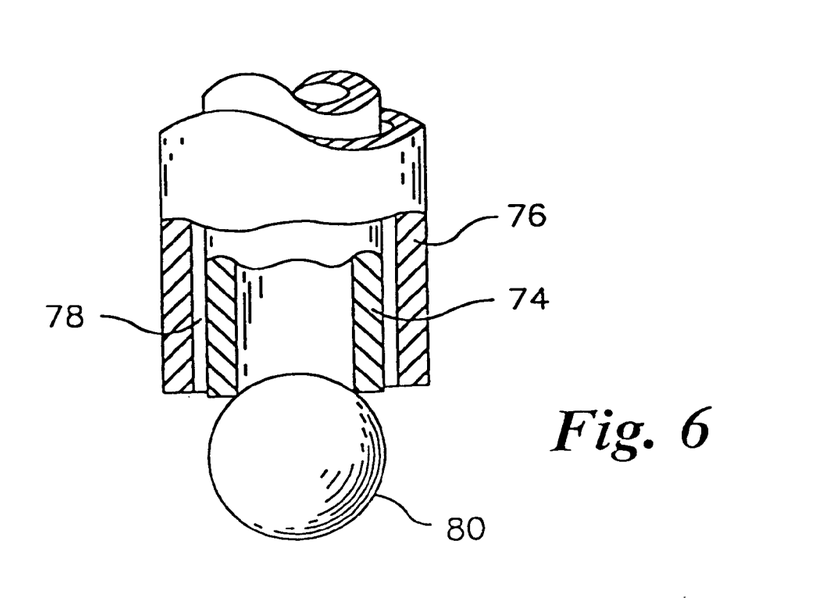
FIG. 6 is a fragmentary sectional view showing a needle having a sheath.

An alternative method of eliminating excess beads is to wash the excess beads from the tip of the needles. This can be done by providing each needle with a coaxial sheath as shown in FIG. 6, where needle 74 is surrounded by a sheath 76, spaced from the outer wall of the needle to provide an annular passage 78. After the sheathed needle is withdrawn from the suspension of beads, with a bead 80 captured at the tip of the needle, a controller causes a momentary flow of solvent outwardly through the annular passage 78 to wash off any excess beads that adhere to the captured bead. Alternatively, a flow of air or other gas through the sheath can be used to dislodge excess beads.

Figure 7:
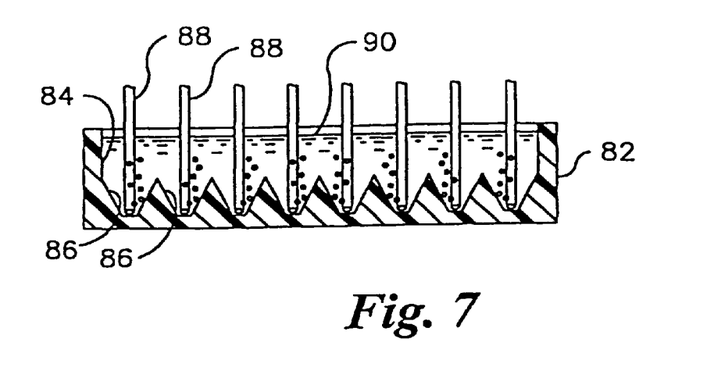
FIG. 7 is a sectional view of an alternative suspension holder.

The tray 24 shown in FIGS. 1 and 2 has separate compartments, one for each needle. The tapered shape of each compartment makes it possible for the beads to be maintained in suspension by the liquid flow induced by rising gas bubbles. The use of separate compartments also allows multiple sub-libraries of beads to be arrayed simultaneously on a well plate. However, it is possible to use gas bubbles to maintain a suspension of a single bead library while capturing and arraying the beads using multiple needles. An arrangement for capturing beads on multiple needles from a single bead library is shown in FIG. 7, in which a tray 82 has a single compartment 84, with a floor formed with multiple tapered recesses 86, each having a gas delivery tube 88 extending to a location adjacent to its bottom. The level of the liquid 90 in the tray is above the peaks defining the tapered recesses in the floor. Consequently, beads in any given recess can rise with the upward liquid flow induced by the rising bubbles, and fall into other recess. This tray can serve any number of bead-capturing needles.

Figure 8:
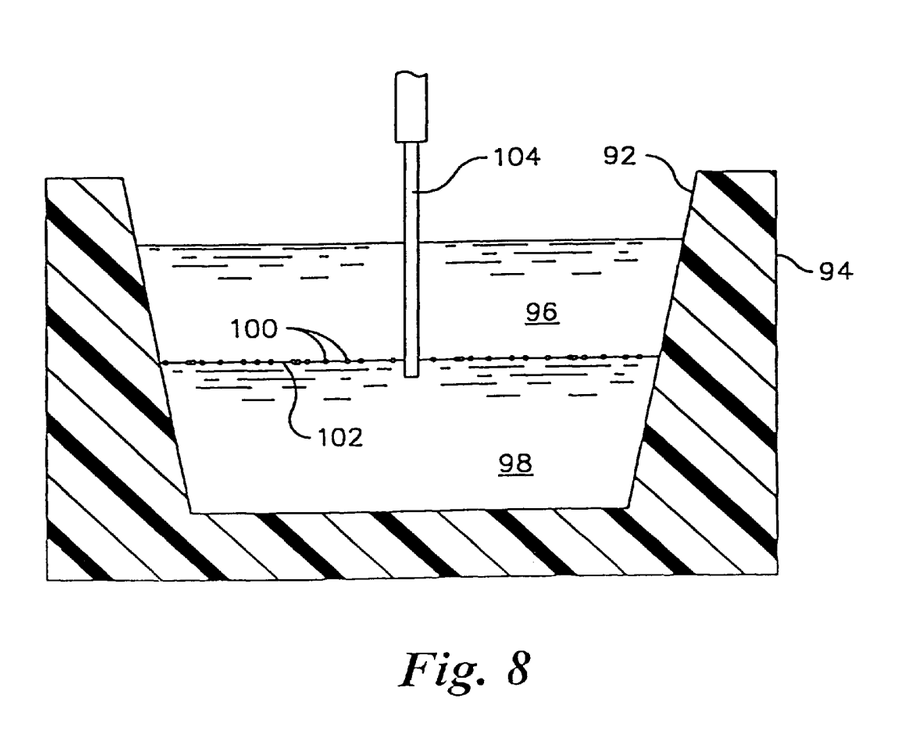
FIG. 8 is a sectional view showing a further alternative suspension holder.

Instead of using rising bubbles to maintain beads in suspension, an alternative, which also avoids breaking up of the beads, is to float the beads on the interface between two immiscible liquids as depicted in FIG. 8. The interior compartment 92 of a tray 94 contains a quantity of toluene 96 floating on a quantity of water 98. Beads 100, which have a density slightly less than that of water, but greater than that of toluene, float on the interface 102 between the two liquids, and can be captured individually by a needle 104 by drawing liquid into the tip 106 of the needle as it passes, either downwardly or upwardly, through the interface.

As will be apparent from the foregoing description, this invention provides a very simple, reliable, inexpensive and easily used apparatus and process for selecting beads individually from a combinatorial library and depositing the selected beads into an array.

Numerous modifications can be made to the apparatus and process described. For example, although the use of hollow needles to capture the beads is presently preferred, it is possible to capture beads at the openings of passages formed in other elements, such as tubes, which are movable into and out of a vessel containing a suspension of beads in liquid, and to wash away excess beads.

The trays for containing the suspensions of beads can be modified in various ways. The gas delivery passages for producing bubbles can be built into the walls of the trays, and the walls of the compartments of the trays can be formed in various shapes. Thus, the compartments can be in the form of circular cones, or can be shaped so that only the lower parts are tapered, while the upper parts of their walls are vertical.

Although the use of rising bubbles or floating the beads on the interface between two immiscible liquids is preferred as a method of maintaining the beads in suspension, it is also possible to maintain the suspension by stirring the liquid slowly, by applying ultrasonic energy to the liquid, or by agitating the vessel in which the liquid is contained.

The number of needles in the robotic manipulator can be modified. For example, in the case of an 8×12 well plate, the number of needles carried by the robotic manipulator arm can be eight. Alternatively, provided that a suitable tray is used to contain the suspension of beads, a still larger number of needles, e.g. 96, can be used, in order to array beads more rapidly.

Instead of using syringes to control the capture and release of beads from the needles, the flow of fluid into and out of the needles can be achieved by suitable vacuum pumps in combination with valved air supplies. Clogging of the needles can be detected by external flow sensing instead of by sensing back pressure. Likewise, bead capture can be sensed by an optical detector instead of by pressure sensing. Finally, instead of jarring excess beads loose, or washing them away by the flow of a fluid through sheaths surrounding the needles, they can be washed away by passing the needles through an auxiliary solvent bath.

Still other modifications can be made to the apparatus and process described without departing from the scope of the invention as defined in the following claims.

What is claimed is:

1. A process for arraying beads which comprises:

establishing, in a vessel, a suspension comprising a mixture of beads in a liquid, and preventing the beads from settling in said vessel;

introducing into said suspension a hollow movable element having an internal passage with an opening at an end thereof, the opening being of a size smaller than any one of the beads, being shaped so that it can be substantially closed off by a bead, and being positioned, when the hollow movable element is introduced into the vessel, at a location within the vessel such that it can be approached and closed off by any one of the beads of said mixture;

drawing liquid from said vessel into said internal passage through said opening and thereby inducing approaching movement of at least one bead toward the opening, until one bead closes off the opening;

when said one bead closes off the opening, establishing a pressure differential such that the external pressure exerted on the bead closing off the opening is greater than the pressure within the passage, thereby holding the bead in engagement with the opening;

withdrawing the movable element from the vessel with the bead in engagement with the opening; and depositing the bead at a location remote from the vessel by releasing the bead from the opening.

2. The process according to claim 1 in which the beads are spherical and the opening is circular.

3. The process according to claim 1 in which, after said one bead closes off the opening at the end of the internal passage of the hollow movable element, the hollow movable element is jarred to dislodge any beads adhering to it other than the one bead closing off the opening.

4. The process according to claim 1 in which, after said one bead closes off the opening at the end of the internal passage of the hollow movable element, a fluid is caused to flow over at least a part of the hollow movable element to dislodge any beads adhering to it other than the one bead closing off the opening.

5. The process according to claim 1 in which the hollow movable element is a needle.

6. A process for arraying beads which comprises:
drawing liquid, from a vessel containing a mixture of beads suspended in a liquid, into an internal passage of a hollow movable element through an opening at an end of the internal passage, the opening being of a size smaller than any one of the beads and being shaped so that it can be substantially closed off by a bead;
when a bead closes off the opening, establishing a pressure differential such that the external pressure exerted on the bead closing off the opening is greater than the pressure within the passage, thereby holding the bead in engagement with the opening;
withdrawing the movable element from the vessel with the bead in engagement with the opening; and
depositing the bead at a location remote from the vessel by releasing the bead from the opening;
in which the hollow movable element comprises a hollow needle extending along an axis and a sheath coaxial with and surrounding the needle, and spaced therefrom to provide an annular passage surrounding the needle, in which the internal passage is a passage within the needle, and in which, after the bead closes off the opening at the end of the internal passage, a fluid is caused to flow through the annular passage to dislodge any beads adhering to the hollow movable element other than the bead closing off the opening.

7. The process according to claim 1 in which the beads of the mixture are held in suspension in the liquid by introducing a flow of gas into the vessel to produce gas bubbles therein.

8. The process according to claim 1 in which at least a portion of the interior of the vessel extending upwardly from the bottom thereof has a continuously increasing horizontal cross-section in the upward direction, and in which the beads of the mixture are held in suspension in the liquid by introducing a flow of gas into the liquid in the vessel at the bottom thereof to produce rising gas bubbles in the liquid.

9. A process for arraying beads which comprises:
drawing liquid, from a vessel containing a mixture of beads suspended in a liquid, into an internal passage of a hollow movable element through an opening at an end of the internal passage, the opening being of a size smaller than any one of the beads and being shaped so that it can be substantially closed off by a bead;
when a bead closes off the opening, establishing a pressure differential such that the external pressure exerted on the bead closing off the opening is greater than the pressure within the passage, thereby holding the bead in engagement with the opening;
withdrawing the movable element from the vessel with the bead in engagement with the opening; and
depositing the bead at a location remote from the vessel by releasing the bead from the opening
in which the liquid in which the beads are suspended comprises two immiscible liquid components, one component floating on the other, in which the density of the beads is higher than the density of the one component and lower than the density of the other component, whereby the beads are suspended at the interface of the two components, and in which the drawing of liquid is carried out as the opening at the end of the internal passage of the hollow movable element is moved through the interface.

10. The process according to claim 1 in which the step of drawing liquid is preceded by applying pressure to gas in the internal passage of the hollow movable element, and sensing flow of gas through said opening in response to the applied pressure, to detect clogging of the internal passage.

11. An apparatus for arraying beads which comprises:
a vessel containing a mixture of beads suspended in a liquid;
means for preventing the beads from settling out of the suspension in said vessel;
a hollow movable element having an internal passage and an opening at an end of the internal passage, the opening being circular in shape so that it can be substantially closed off by a spherical bead;
means for introducing the hollow movable element into the suspension and positioning the opening within the suspension at a location such that it can be approached and closed off by any one of the beads of the mixture;
means for drawing liquid from the vessel into the internal passage of the hollow movable element through the opening, for establishing a pressure differential such that the external pressure exerted on the bead closing off the opening is greater than the pressure within the passage, thereby holding the bead in engagement with the opening, and for depositing the bead at a location remote from the vessel by releasing the bead from the opening; and
means for withdrawing the movable element from the vessel with the bead in engagement with the opening and for moving the movable element to said remote location.

12. A process for arraying beads which comprises:
establishing, in a vessel, a suspension comprising a mixture of beads in a liquid, and preventing the beads from settling in said vessel by introducing a flow of gas into the vessel to produce gas bubbles therein or by maintaining, in the vessel, two immiscible liquid components, one component floating on the other, in which the density of the beads is higher than the density of the one component and lower than the density of the other component, whereby the beads are suspended at the interface of the two components;
drawing liquid, from said vessel into an internal passage of a hollow movable element through an opening at an end of the internal passage, the opening being of a size smaller than any one of the beads and being shaped so that it can be substantially closed off by a bead;
when a bead closes off the opening, establishing a pressure differential such that the external pressure exerted on the bead closing off the opening is greater than the pressure within the passage, thereby holding the bead in engagement with the opening;

withdrawing the movable element from the vessel with the bead in engagement with the opening; and depositing the bead at a location remote from the vessel by releasing the bead from the opening.

13. A process according to claim 12 in which the step of preventing the beads from settling in said vessel is carried out by introducing a flow of gas into the vessel to produce gas bubbles therein.

14. A process according to claim 12 in which the step of preventing the beads from settling in said vessel is carried out by maintaining, in the vessel, two immiscible liquid components, one component floating on the other, in which the density of the beads is higher than the density of the one component and lower than the density of the other component, whereby the beads are suspended at the interface of the two components.

15. An apparatus for arraying beads which comprises:

a vessel containing a mixture of beads suspended in a liquid;

means for preventing the beads from settling out of the suspension in said vessel said preventing means comprising means for introducing a flow of gas into the vessel to produce gas bubbles therein or means for maintaining, in the vessel, two immiscible liquid components, one component floating on the other, in which the density of the beads is higher than the density of the one component and lower than the density of the other component, whereby the beads are suspended at the interface of the two components;

a hollow movable element having an internal passage and an opening at an end of the internal passage, the opening being circular in shape so that it can be substantially closed off by a spherical bead;

means for drawing liquid from the vessel into the internal passage of the hollow movable element through the opening, for establishing a pressure differential such that the external pressure exerted on the bead closing off the opening is greater than the pressure within the passage, thereby holding the bead in engagement with the opening, and for depositing the bead at a location remote from the vessel by releasing the bead from the opening; and means for withdrawing the movable element from the vessel with the bead in engagement with the opening and for moving the movable element to said remote location.

16. An apparatus according to claim 15 in which the means for preventing the beads from settling out of the suspension comprises means for introducing a flow of gas into the vessel to produce gas bubbles therein.

17. An apparatus according to claim 15 in which the means for preventing the beads from settling out of the suspension comprises means for maintaining, in the vessel, two immiscible liquid components, one component floating on the other, in which the density of the beads is higher than the density of the one component and lower than the density of the other component, whereby the beads are suspended at the interface of the two components.

* * * * *